(12) United States Patent
Heberle et al.

(10) Patent No.: US 11,581,696 B2
(45) Date of Patent: Feb. 14, 2023

(54) MULTI-CHANNEL LASER

(71) Applicant: Open Water Internet Inc., San Francisco, CA (US)

(72) Inventors: Albert P. Heberle, Santa Clara, CA (US); Gregory Lee Keaton, San Francisco, CA (US); Mary Lou Jepsen, Sausalito, CA (US); Craig Newswanger, Oakland, CA (US); Hosain Haghany, San Francisco, CA (US)

(73) Assignee: Open Water Internet Inc., San Francisco, CA (US)

( * ) Notice: Subject to any disclaimer, the term of this patent is extended or adjusted under 35 U.S.C. 154(b) by 698 days.

(21) Appl. No.: 16/540,514

(22) Filed: Aug. 14, 2019

(65) Prior Publication Data
US 2021/0050704 A1  Feb. 18, 2021

(51) Int. Cl.
| H01S 3/00 | (2006.01) |
| H01S 3/067 | (2006.01) |
| A61B 5/00 | (2006.01) |
| H01S 3/30 | (2006.01) |
| H01S 3/10 | (2006.01) |
| H01S 5/062 | (2006.01) |

(52) U.S. Cl.
CPC ............ *H01S 3/302* (2013.01); *A61B 5/0035* (2013.01); *A61B 5/0042* (2013.01); *A61B 5/745* (2013.01); *H01S 3/0085* (2013.01); *H01S 3/06712* (2013.01); *H01S 3/06754* (2013.01); *H01S 3/10015* (2013.01); *H01S 5/0622* (2013.01); *A61B 2562/046* (2013.01)

(58) Field of Classification Search
CPC ...... H01S 5/50; H01S 5/4015; H01S 3/06754; A61B 5/0035; A61B 5/0042
See application file for complete search history.

(56) References Cited

U.S. PATENT DOCUMENTS

| 5,121,400 A * | 6/1992 | Verdiell ................. G02F 1/397 372/71 |
| 5,409,479 A | 4/1995 | Dew et al. |
| 5,887,009 A | 3/1999 | Mandella et al. |
| 6,172,760 B1 | 1/2001 | Son |
| 6,200,309 B1 | 3/2001 | Rice et al. |
| 6,304,328 B1 | 10/2001 | Longtin |

(Continued)

OTHER PUBLICATIONS

Patent Cooperation Treaty, International Searching Authority, International Application No. PCT/US2019/046226, Notification Date: Nov. 9, 2020, 3 pages.

(Continued)

*Primary Examiner* — Eric L Bolda
(74) *Attorney, Agent, or Firm* — Freestone Intellectual Property Law PLLC; Aaron J. Visbeek

(57) ABSTRACT

A laser device includes a seed laser, a plurality of optical amplifiers, and an optical distribution assembly. The seed laser is configured to emit seed laser light. The plurality of optical amplifiers is configured to generate amplified laser light by amplifying the seed laser light. The optical distribution assembly is configured to distribute the seed laser light to an input of each of the optical amplifiers in the plurality and each of the optical amplifiers is configured to direct its respective amplified laser light to a common target.

20 Claims, 8 Drawing Sheets

(56) References Cited

U.S. PATENT DOCUMENTS

| | | |
|---|---|---|
| 6,624,925 B2 | 9/2003 | Hasson et al. |
| 6,956,650 B2 | 10/2005 | Boas |
| 7,119,906 B2 | 10/2006 | Pepper |
| 7,460,248 B2 | 12/2008 | Kurtz |
| 7,551,809 B2 | 6/2009 | Taira |
| 7,610,082 B2 | 10/2009 | Chance |
| 7,647,091 B2 | 1/2010 | Ntziachristos |
| 7,728,986 B2 | 6/2010 | Lasker |
| 7,804,070 B1 | 9/2010 | Pan |
| 7,821,640 B2 | 10/2010 | Koenig |
| 7,822,468 B2 | 10/2010 | Stammes |
| 7,826,878 B2 | 11/2010 | Alfano |
| 7,898,649 B2 | 3/2011 | Masumura |
| 7,965,389 B2 | 6/2011 | Da Silva |
| 7,983,740 B2 | 7/2011 | Culver |
| 7,928,896 B2 | 8/2011 | Jin |
| 8,014,847 B2 | 9/2011 | Shastri |
| 8,120,784 B2 | 2/2012 | Da Silva |
| 8,170,651 B2 | 5/2012 | Lorenzo |
| 8,239,006 B2 | 8/2012 | Zhu |
| 8,263,947 B2 | 9/2012 | Da Silva |
| 8,289,502 B2 | 10/2012 | Yoshida |
| 8,326,567 B2 | 12/2012 | Masumura |
| 8,330,642 B2 | 12/2012 | Jin |
| 8,355,131 B2 | 1/2013 | Bakker |
| 8,357,915 B2 | 1/2013 | Guyon |
| 8,374,409 B2 | 2/2013 | Jochemsen |
| 8,416,421 B2 | 4/2013 | Wang |
| 8,450,674 B2 | 5/2013 | Yang |
| 8,451,450 B2 | 5/2013 | Heng |
| 8,520,921 B2 | 8/2013 | Ziegler |
| 8,525,998 B2 | 9/2013 | Yaqoob |
| 8,527,242 B2 | 9/2013 | Granot |
| 8,531,662 B2 | 9/2013 | Van Der Mark |
| 8,563,932 B2 | 10/2013 | Fang |
| 8,634,077 B2 | 1/2014 | Hu |
| 8,649,015 B2 | 2/2014 | Ichihara |
| 8,917,442 B2 | 3/2014 | Baym |
| 8,717,574 B2 | 5/2014 | Yang |
| 8,814,795 B2 | 8/2014 | Derode |
| 8,817,255 B2 | 8/2014 | Masumura |
| 8,830,573 B2 | 9/2014 | Cui |
| 8,847,175 B2 | 9/2014 | Laidevant |
| 8,937,284 B2 | 1/2015 | Fang |
| 8,954,130 B2 | 2/2015 | Masumura |
| 8,976,433 B2 | 3/2015 | Masumura |
| 9,012,869 B2 | 4/2015 | Andersson-Engels |
| 9,036,970 B2 | 5/2015 | Guyon |
| 9,037,216 B2 | 5/2015 | Hielscher |
| 9,057,695 B2 | 6/2015 | Masumura |
| 9,131,851 B2 | 9/2015 | Fukutani |
| 9,134,229 B2 | 9/2015 | Lesage |
| 9,179,842 B2 | 11/2015 | Nakaji |
| 9,207,171 B2 | 12/2015 | Nadakuditi |
| 9,234,841 B2 | 1/2016 | Wang |
| 9,282,932 B2 | 3/2016 | Kudo |
| 9,297,752 B2 | 3/2016 | Shimokawa |
| 9,304,490 B2 | 4/2016 | Masumura |
| 9,313,423 B2 | 4/2016 | Wang |
| 9,335,604 B2 | 5/2016 | Popovich |
| 9,335,605 B2 | 5/2016 | Wang |
| 9,341,569 B2 | 5/2016 | T Hooft |
| 9,354,166 B2 | 5/2016 | Judkewitz |
| 9,373,020 B2 | 6/2016 | Kudo |
| 9,407,796 B2 | 8/2016 | Dinten |
| 9,427,213 B2 | 8/2016 | Suzuki |
| 9,480,425 B2 | 11/2016 | Culver |
| 9,486,142 B2 | 11/2016 | Hielscher |
| 9,488,574 B2 | 11/2016 | Koehler |
| 9,509,956 B2 | 11/2016 | Piestun |
| 9,622,663 B2 | 4/2017 | Fang |
| 9,689,797 B2 | 6/2017 | Sun |
| 9,724,489 B2 | 8/2017 | Barbour |
| 9,730,649 B1 * | 8/2017 | Jepsen ............... A61B 8/5261 |
| 9,750,413 B2 | 9/2017 | Sandusky |
| 2004/0150818 A1 | 8/2004 | Armstrong et al. |
| 2005/0128569 A1 * | 6/2005 | Park .................... H01S 5/50 |
| | | 359/333 |
| 2005/0271094 A1 | 12/2005 | Miller et al. |
| 2006/0253007 A1 | 11/2006 | Cheng et al. |
| 2007/0008609 A1 | 1/2007 | Ohtsuki et al. |
| 2007/0229939 A1 | 10/2007 | Brown et al. |
| 2009/0201575 A1 * | 8/2009 | Fermann ........... H01S 3/06745 |
| | | 359/341.32 |
| 2010/0016732 A1 | 1/2010 | Wells |
| 2012/0070817 A1 | 3/2012 | Wang |
| 2014/0081096 A1 | 3/2014 | Baym |
| 2014/0114181 A1 | 4/2014 | Wu |
| 2014/0303473 A1 | 10/2014 | Nanaumi |
| 2015/0182121 A1 | 7/2015 | Barbour |
| 2015/0238092 A1 | 8/2015 | Masumura |
| 2015/0241342 A1 | 8/2015 | Zhou |
| 2015/0346027 A1 | 12/2015 | Khare |
| 2015/0351635 A1 | 12/2015 | Cerussi |
| 2016/0085135 A1 | 3/2016 | Park |
| 2016/0139266 A1 | 5/2016 | Montoya et al. |
| 2016/0157723 A1 | 6/2016 | Kanick |
| 2016/0262723 A1 | 9/2016 | Zhu |
| 2016/0363527 A1 | 12/2016 | Ruan |
| 2016/0365693 A1 | 12/2016 | Chuang et al. |
| 2017/0118423 A1 | 4/2017 | Zhou |
| 2017/0163946 A1 | 6/2017 | Komanduri |
| 2017/0168565 A1 | 6/2017 | Cohen |
| 2017/0202633 A1 | 7/2017 | Liu |
| 2017/0230555 A1 | 8/2017 | Tabirian |
| 2017/0231501 A1 | 8/2017 | Culver |
| 2017/0299697 A1 | 10/2017 | Swanson |
| 2018/0317776 A1 | 11/2018 | Islam |
| 2020/0089165 A1 * | 3/2020 | Delgado ............. G03H 1/0465 |
| 2021/0153743 A1 * | 5/2021 | Morales Delgado ............... |
| | | G03H 1/0443 |
| 2021/0333565 A1 * | 10/2021 | Limpert ............. H01S 3/0071 |

OTHER PUBLICATIONS

Patent Cooperation Treaty, Notification of Transmittal of the International Search Report and the Written Option of the International Searching Authority, or the Declaration, International Application No. PCT/US2020/046226, dated Nov. 9, 2020, 1 page.

Patent Cooperation Treaty, Written Opinion of the International Searching Authority, International Application No. PCT/US2020/046226, dated Nov. 9, 2020, 7 pages.

Arridge et al. Nonuniqueness in diffusion-based optical tomography, Optics Letters, Jun. 1, 1998, vol. 23, No. 11, pp. 882-884.

Hofmann et al. Differential light detector, Rev. Sci. Instrum, Feb. 1979, vol. 50, No. 2, pp. 249-252.

Freund et al. Memory Effects in Propagation of Ooptical Waves through Disordered Media, Physical Review Letters, Nov. 14, 1988, vol. 61, No. 20, pp. 2328-2331.

Goodman et al. Wavefront-Reconstruction Imaging Through Random Media, Jun. 15, 1966, vol. 8, No. 12, pp. 311-313.

Peng et al. Low loss liquid crystals for infrared applications, Liquid Crystal, 2014, vol. 41, No. 11, pp. 1545-1552.

\* cited by examiner

MULTI-CHANNEL LASER

BACKGROUND INFORMATION

Imaging devices are used in contexts such as healthcare, navigation, and security, among others. Imaging systems often measure radio waves or light waves to facilitate imaging. Imaging that measures light scattered by an object is especially challenging and advances to the devices, systems, and methods to improve optical imaging are sought to increase speed, increase resolution, reduce size and/or reduce cost. Some imaging systems require high-intensity light sources and may require laser light sources due to the specific features of laser light (e.g. spatial and/or temporal coherence). Other contexts may also require high-intensity laser light having particular high-power light requirements.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

DETAILED DESCRIPTION

Figure 1A:
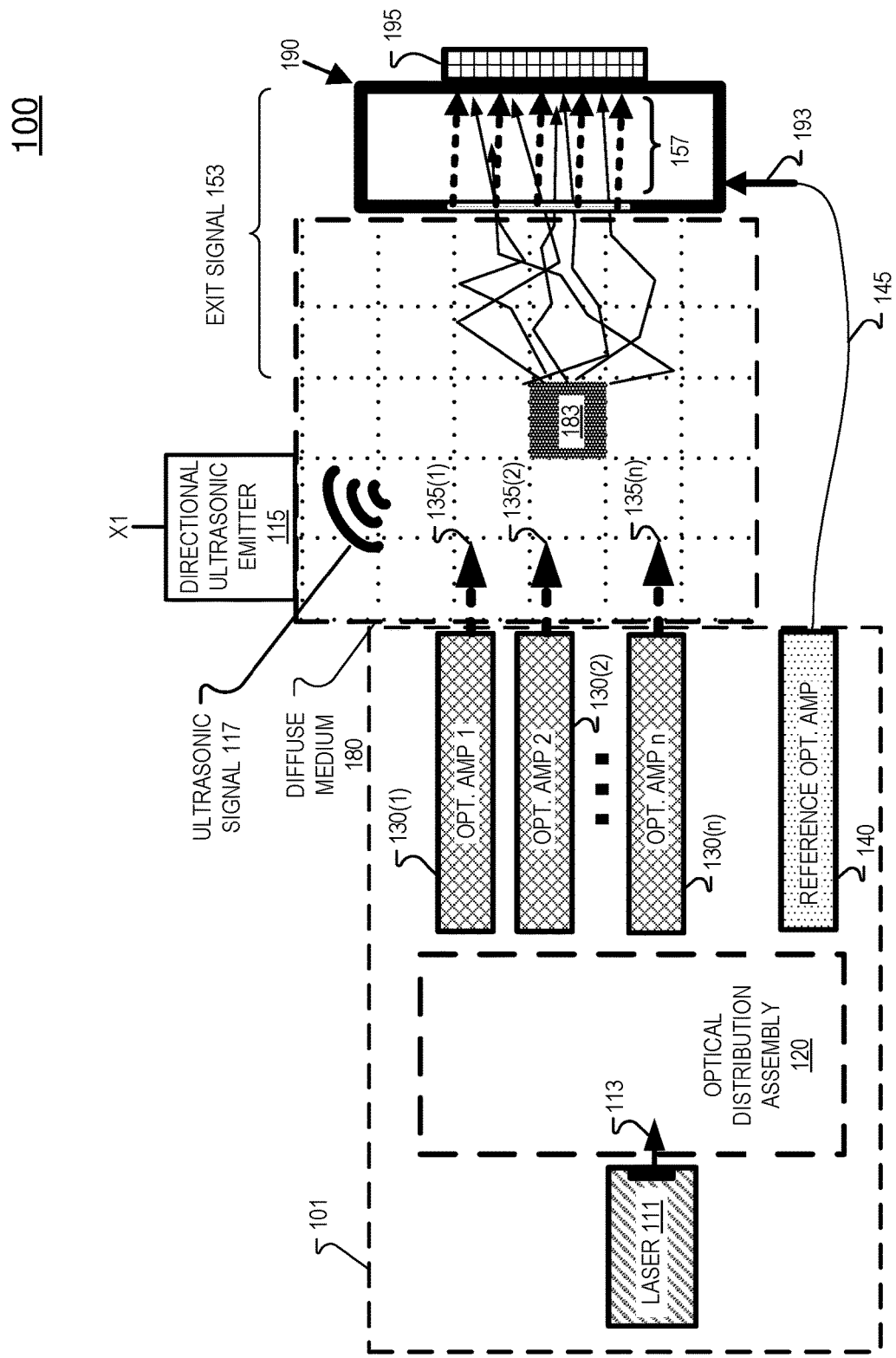
FIG. 1A illustrates an imaging device including an imaging module and a laser assembly, in accordance with aspects of the disclosure.

Embodiments of a laser device and an imaging device are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

This disclosure will generally describe imaging a diffuse medium in the context of human tissue in the medical context, however, the content of this disclosure may be applied to medical imaging, navigation, security, scientific research, or other contexts that image diffuse mediums or objects.

Human tissue is translucent to infrared light, although different parts of the human body (e.g. skin, blood, bone) exhibit different absorption and scattering coefficients. Researchers have attempted to use the properties of infrared light for medical imaging purposes, but size and cost constraints have been prohibitive for wide-scale adoption. Illuminating tissue and other diffuse media with near-infrared light for imaging purposes is sometimes referred to as Diffuse Optical Tomography. In one Diffuse Optical Tomography technique, time-of-flight (TOF) imaging can theoretically be employed by measuring the time it takes for "ballistic" photons (those photons that are not scattered) to pass through tissue. Since the ballistic photons reach the sensor the fastest, they are the least impeded (have the shortest optical path) and thus some conclusion can be drawn to create an image of the tissue that is illuminated by infrared light. However, TOF imaging generally requires specialty hardware (e.g. picosecond pulsed lasers and single photon detectors) to facilitate ultrafast shutters on sensors that are able to image at the speed of light and the systems are overall very expensive and bulky. TOF imaging also requires an input of approximately 10-100 fold (or more) light intensity into the body than is used at the detector; thus efficacy and power limitations as well as safety limits on input intensity limit TOF imaging resolution and utility.

In contrast to TOF imaging, some embodiments of this disclosure may illuminate a diffuse medium with an infrared illumination light while an ultrasound emitter is focusing an ultrasonic signal on a particular voxel. The infrared illumination light encountering the particular voxel may be wavelength-shifted by the ultrasonic signal and thus form a wavelength-shifted exit signal that exits the diffuse medium. A light detector (e.g. photodiode, array of photodiodes, or image pixel array) may capture a signal (e.g. an image) of an interference between the wavelength-shifted exit signal and an infrared reference beam having the same wavelength as the wavelength-shifted exit signal. The signal of the interference between the wavelength-shifted exit signal and an infrared reference beam can be used to measure an absorption value of the particular voxel. In one example, a Fourier transform of an image of the interference pattern between the wavelength-shifted exit signal and an infrared reference beam generates an absorption value for the particular voxel. As the ultrasound emitter raster-scans to different voxels and absorption values for different voxels are generated, the absorption values can be aggregated to generate a two-dimensional or three-dimensional image of the diffuse medium.

The infrared illumination light for illuminating a diffuse medium such as tissue may have particular requirements that are not easily generated. For example, it may be advantageous for the infrared illumination light to have a particular line-width. It may be advantageous for the infrared illumination light to be pulsed laser light (rather than continuous-wave) where a high-intensity pulse is delivered over a short period of time (e.g. 250 ns). Example conventional laser designs for achieving high-intensity laser light includes amplifying laser light via optical amplification where the laser light propagates down a single common optical fiber. This approach can be problematic at certain power-thresholds as high-power laser light propagating along a single optical fiber suffers from stimulated Brillouin scattering that erodes the intensity of the laser light. If parallel optical amplifiers are used to generate high-intensity laser light, the outputs of the parallel optical amplifiers are coupled together to a common laser light output so that the amplified laser beam retains a particular spatial and/or temporal coherence within the same amplified laser beam. However, embodiments of the disclosure may include a laser device that include a plurality of optical amplifiers for amplifying seed laser light where the outputs of the optical amplifiers are not coupled to a common output. Rather, respective amplified laser light emitted by each optical amplifier is directed to a common target (e.g. a diffuse medium). In most any other contexts, separately emitting the amplified laser light from the output of different optical amplifiers to a common target fails to achieve the desired light output characteristics. However, in the context of optical imaging, directing separate, yet synchronized amplified laser light to a common diffuse medium may provide an illumination light of the diffuse medium that meets the requirements (e.g. high-power, short pulse, narrow line-width) of the imaging system. These embodiments and others will be described in more detail with references to FIGS. 1A-8.

FIG. 1A illustrates an imaging device including an imaging module 190 and a laser assembly 101, in accordance with aspects of the disclosure. Imaging device 100 may optionally include directional ultrasonic emitter 115 configured to deliver an ultrasonic signal 117 to a given voxel (e.g. voxel 183) of the diffuse medium 180. Laser assembly 101 includes a seed laser 111, an optical distribution assembly 120, a plurality of optical amplifiers 130, and reference optical amplifier 140. Seed laser 111 is configured to emit seed infrared laser light 113. Seed laser 111 may be a fiber laser or a semiconductor laser, for example. Seed laser 111 may have a power between 0.01 W and 5 W, in some examples. Seed laser 111 may be a continuous wave (CW) laser or a pulsed laser. Optical distribution assembly 120 is configured to receive seed infrared laser light 113 and distribute the seed infrared laser light 113 to inputs of the optical amplifiers 130. Optical amplifiers 130 are configured to generate amplified infrared laser light 130 by amplifying the seed infrared laser light distributed to the optical amplifiers by optical distribution assembly 120.

Optical amplifiers 130 may utilize semiconductor or fiber laser amplifiers, for example. Optical amplifiers 130 may be identical in some embodiments so that the characteristics of their respective amplified infrared laser light are the same or very similar. In some embodiments, an electrical drive current that drives each of the plurality of optical amplifiers is synced so that the amplified infrared laser light 135(1), 135(2) . . . 135(n) are synchronized. This may assist in ensuring that the optical amplifiers are mutually phase-stable when amplified infrared laser light 135 is illuminating the diffuse medium so that the illumination of diffuse medium 180 is by light having identical or almost identical characteristics. For example, if the optical amplifiers are not mutually phase-stable, the different amplified infrared laser lights 135 may have slightly different wavelengths or line-widths. Each optical amplifier 130 may have a power in the range of 1-50 Watts. The output aperture of the optical amplifiers 130 may have a wider taper than conventional optical amplifiers because the beam quality of light 135 that is illuminating the diffuse medium target can have an $M^2$ parameter (beam quality factor) that is very high (e.g. more than 1,000 or even in the millions) while still being suitable as the illumination light for purposes of imaging device 100. In contrast, conventional lasers in a fiber-optic communications context strive for an $M^2$ of close to 1. In embodiments that include reference optical amplifier 140, the reference optical amplifier 140 may have an output aperture taper that supports an $M^2$ that is closer to 1 so that reference light 143 can be coupled into fiber optic 145.

Each of the optical amplifiers is configured to direct its respective amplified infrared laser light 135 into diffuse medium 180 to as infrared illumination light to ultimately generate infrared exit signal 153. In one embodiment, the amplified infrared laser light 135 has a line-width of 1 nm or less and has a wavelength between 680 nm and 1000 nm. In one embodiment, the amplified infrared laser light 135 has a line-width of 1 nm or less and has a wavelength between 1500 nm and 1700 nm.

Directional ultrasonic emitter 115 may be configured to deliver an ultrasonic signal 117 to a given voxel (e.g. voxel 183) of the diffuse medium 180 while the amplified infrared laser light 135 from the plurality of optical amplifiers 130 illuminates the given voxel. Ultrasonic emitter 115 is configured to focus an ultrasonic signal 117 to a point in three-dimensional space. Ultrasonic emitter 115 may utilize a phase-array ultrasound architecture. In the medical context, ultrasonic emitter 115 may be configured to focus an ultrasonic signal 117 to a voxel within the human body. The voxel may be within the brain, abdomen, or uterus, for example. In some embodiments, ultrasonic signal 117 is a plane wave or a linear combination of waves (orthogonal system).

Amplified infrared laser light 135 collectively scatters (scattering not illustrated) within diffuse medium 180 and a portion of the amplified infrared laser light will propagate through voxel 183. In FIG. 1A ultrasonic signal 117 may be focused to voxel 183 which represents a small three-dimensional segment of diffuse medium 180. The amplified infrared laser light 135 that propagates through voxel 183 may be wavelength-shifted by the ultrasonic signal 117 and exit diffuse medium 180 as infrared exit signal 153 into imaging module 190.

Figure 1B:
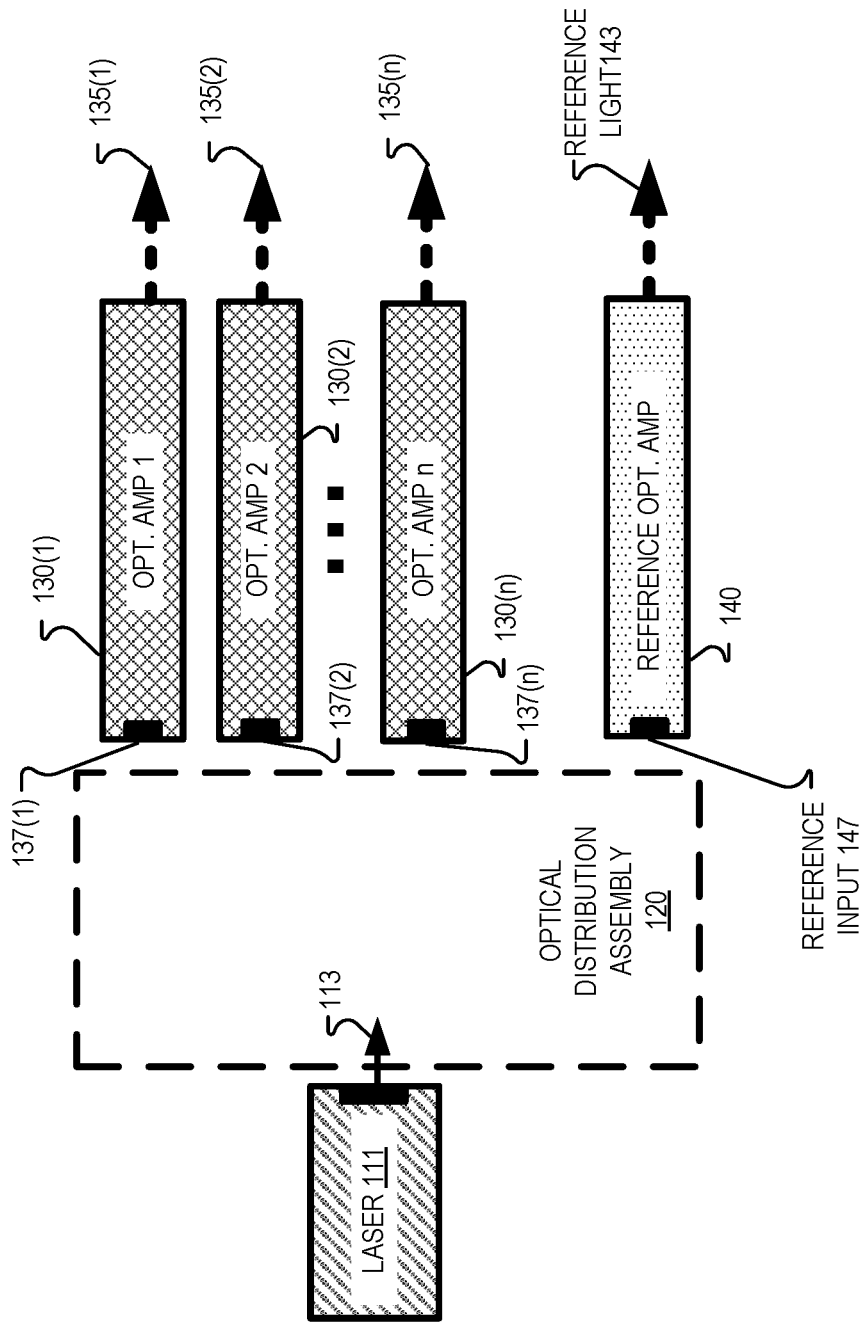
FIG. 1B illustrates a plurality of n optical amplifiers, in accordance with aspects of the disclosure.

In FIG. 1B, the plurality of optical amplifiers includes optical amplifiers 130(1), 130(2) . . . 130(n), where n is an integer number. Integer number n may be 10, 16, 25, 100 or more, in some embodiments. That is, laser assembly 101 may include 10, 16, 14, 100, or more optical amplifiers 130 that receive seed infrared laser light 113 at the inputs 137 of the optical amplifiers 130 and the optical amplifiers 130 in the plurality will emit amplified laser light 135 to illuminate diffuse medium 180. In some embodiments, each optical amplifier 130 may include a frequency converter configured to down-convert a first wavelength of the seed infrared laser light (e.g. 1550 nm) to a second wavelength (e.g. 775 nm) so that the amplified laser light 135 has a shorter wavelength than a wavelength of seed infrared laser light 113.

FIG. 1B illustrates that in some embodiments, reference optical amplifier 140 may be included in laser assembly 101 and reference optical amplifier 140 may generate infrared reference light 143 at the output of reference optical amplifier 140 to be provided to imaging module 190. In some embodiments, the infrared reference light 143 is provided to imaging module 190 via fiber optic 145. In some embodiments, a wavelength-shifting module is coupled between reference optical amplifier 140 and input 193 of imaging module 190. In these embodiments, the wavelength-shifting module may shift the wavelength of the infrared reference light 143 to have the same wavelength as infrared exit signal 153. In one embodiment, a wavelength-shifting module is positioned prior to reference optical amplifier 140. In one embodiment, the wavelength-shifting module includes an acoustic-optical-modulator (AOM). In FIG. 1B, optical distribution assembly 120 is configured to distribute the seed infrared laser light 113 to a reference input 147 of reference optical amplifier 140. In some embodiments, reference optical amplifier 147 is not included and a portion of the seed infrared laser light 113 is provided to input 193 (unamplified) as infrared reference light.

Referring again to FIG. 1A, imaging module 190 includes a sensor 195 configured to image an interference pattern generated by an infrared reference beam 157 interfering with infrared exit signal 153. Sensor 195 may be implemented with an a-Si (amorphous Silicon) thin film transistors, in some embodiments or a CMOS (Complementary Metal-Oxide-Semiconductor) image sensor, in some embodiments. In some embodiments, sensor 195 may include a charge-coupled device (CCD). Sensor 195 can be a commercially available image sensor. In one embodiment, the image sensor has image pixels having a pixel pitch of 3.45 microns. In one embodiment, the image sensor has image pixels having a pixel pitch of 1.67 microns. In one embodiment, the image sensor has image pixels having a pixel pitch of one micron or less. The pixel resolution of the image sensor may vary depending on the application. In one embodiment, the image sensor is 1920 pixels by 1080 pixels. In one embodiment, the image sensor is 40 Megapixels or more.

Figure 2:
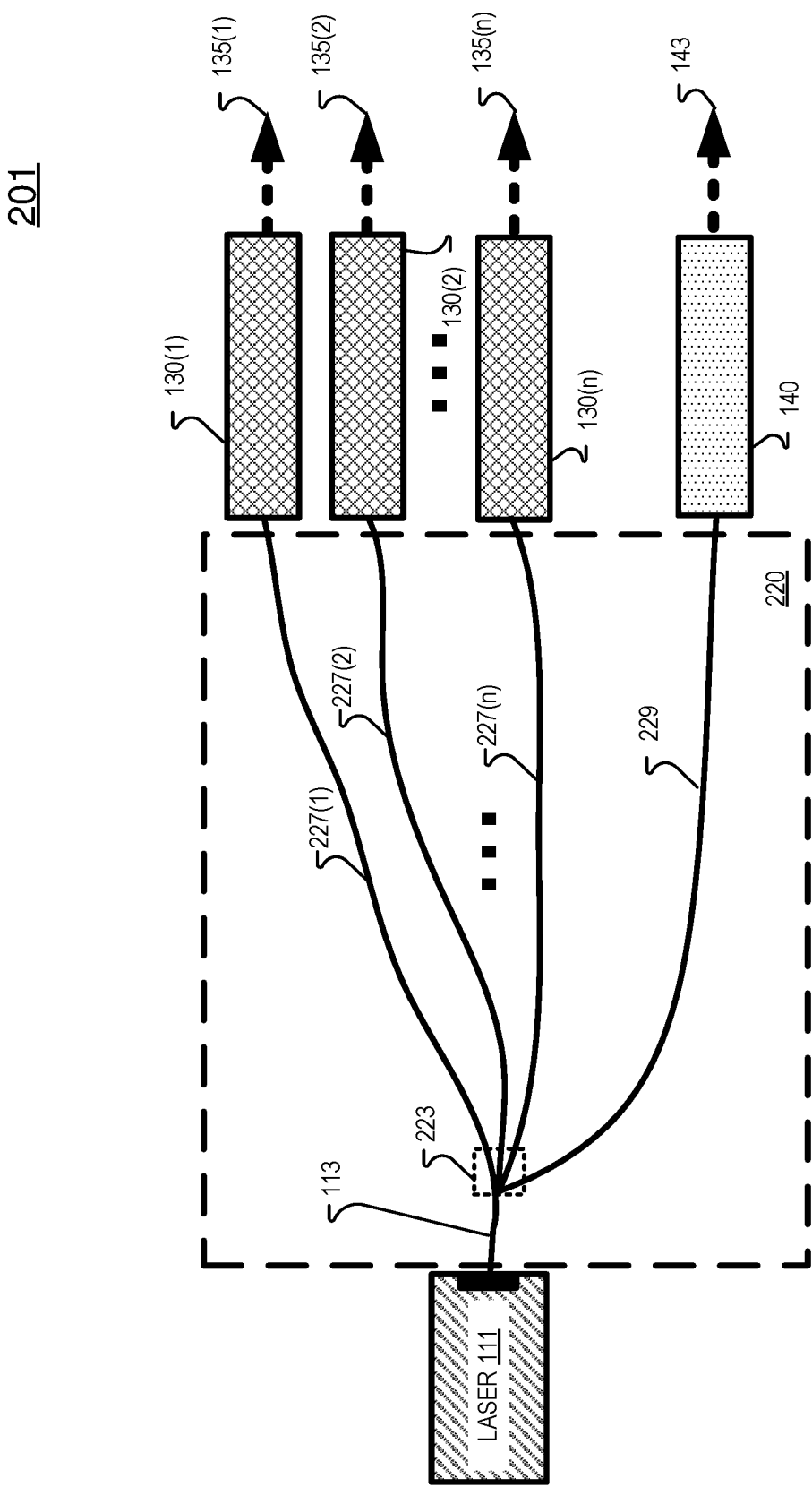
FIG. 2 illustrates an example laser assembly that includes an example optical distribution assembly, in accordance with aspects of the disclosure.

FIG. 2 illustrates an example laser assembly 201 that includes an example optical distribution assembly 220, in accordance with aspects of the disclosure. Optical distribution assembly 220 includes a plurality of optical fibers 227 configured to guide portions of the seed infrared laser light 113 to the plurality of optical amplifiers 130. Coupler 223 may divide the seed infrared laser light 113 between the respective optical fibers 227. In some embodiments, seed infrared laser light 113 is divided equally between optical fibers 227. Coupler 223 may be a fiber splitter or a diffractive optical splitter, for example. In FIG. 2, optical fiber 227(1) delivers the first portion of the seed infrared laser light 113 to optical amplifier 130(1), optical fiber 227(2) delivers the second portion of the seed infrared laser light 113 to optical amplifier 130(2) . . . and optical fiber 227(n) delivers the $n^{th}$ portion of the seed infrared laser light 113 to optical amplifier 130(n). Optical fiber 229 may optionally provide a portion of seed infrared laser light 113 to reference optical amplifier 140.

Figure 3:
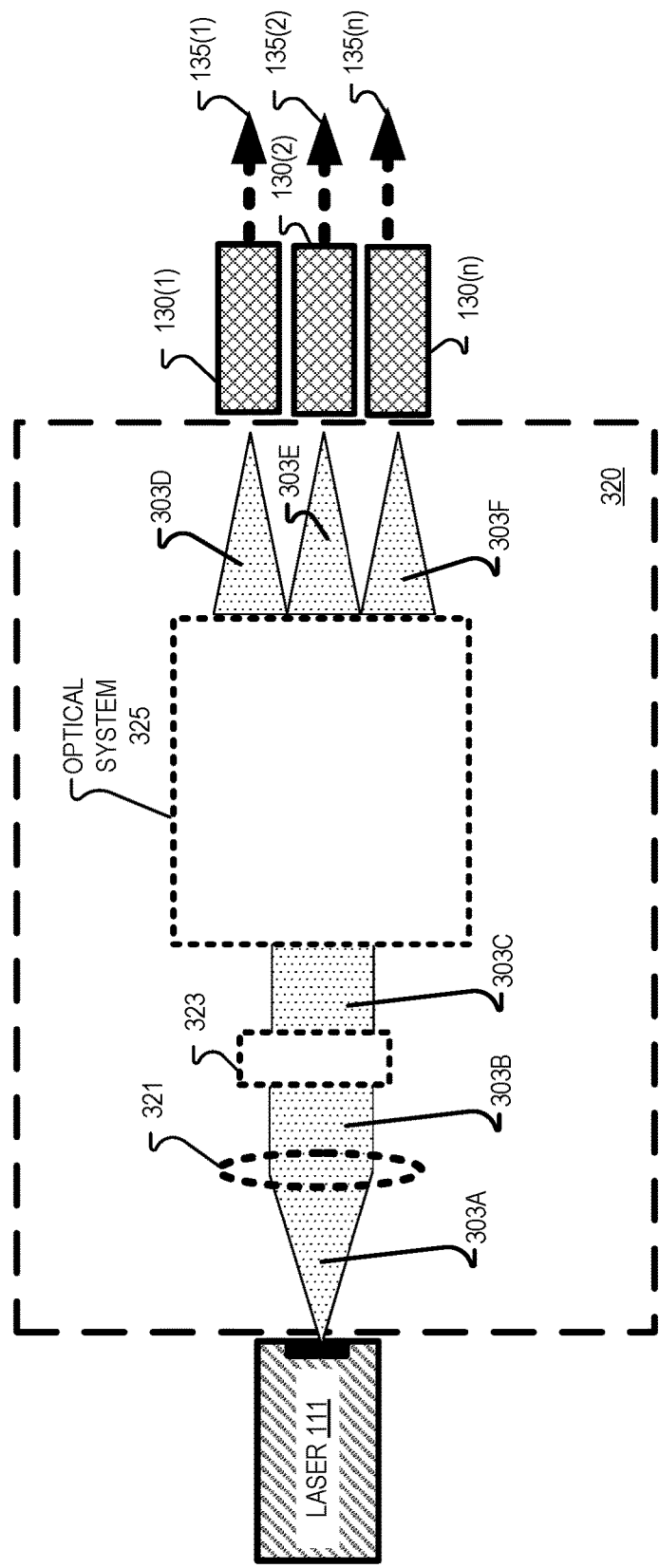
FIG. 3 illustrates an example laser assembly that includes an example optical distribution assembly, in accordance with aspects of the disclosure.

FIG. 3 illustrates an example laser assembly 301 that includes an example optical distribution assembly 320, in accordance with aspects of the disclosure. Example optical distribution assembly 320 includes an optical isolator 323 configured to receive seed infrared laser light 303A from seed laser 111. Optical isolator 323 prevents seed laser 111 from receiving (potentially harmful) optical feedback from the rest of the optical system that is downstream from optical isolator 323. Optical isolator 323 may include a linear polarizer, a Faraday rotator, a second linear polarizer rotated 45 degrees, and a half wave plate at 22.5 degrees to compensate for the 45 degree rotation of the Faraday rotator. In FIG. 3, an optional collimating optical element 321 is disposed between optical isolator 323 and seed laser 111 to collimate seed infrared laser light 303A into collimated seed infrared laser light 303B prior to the seed infrared laser light propagating to optical isolator 323. Collimating optical element 321 may be a refractive or diffractive lens. Light 303C is seed infrared laser light that has been isolated by optical isolator 323 and is received by optical system 325.

Optical system 325 is configured to generate distributed beams illuminating the inputs of optical amplifiers 130. In FIG. 3, distributed beam 303D illuminates an input to optical amplifier 130(1), distributed beam 303E illuminates an input to optical amplifier 130(2) . . . and distributed beam 303F illuminates an input to optical amplifier 130(n). Each of the distributed beams may have approximately the same intensity. Optical system 325 may be configured to generate a one-dimensional array of distributed beams or a two-dimensional array of distributed beams, depending on the spatial orientation of the inputs 137 of optical amplifiers 130. Optical system 325 may include a single holographic optical element that receives light 303C and generates the appropriate number of distributed beams to illuminate the inputs of the optical amplifiers. Optical system 325 may include a network of mirrors, reflective lenses, and/or refractive lenses to generate the distributed beams. In some embodiments, optical system 325 includes a plurality of photonic integrated circuits that can generate the distributed beams. Although not illustrated specifically in FIG. 3, optical system 325 may generate a distributed beam to illuminate an input 147 of reference optical amplifier 140, in some embodiments. In some embodiments, reference optical amplifier 140 receives seed infrared laser light 303, but not from optical system 325. For example, reference optical amplifier 140 may receive a portion of seed infrared laser light 303 from an optical fiber receiving the seed infrared laser light upstream of optical system 325 (between optical system 325 and seed laser 111). The intensity of the seed infrared laser light 303 that is provided to reference optical amplifier 140 may be different from the intensities provided to optical amplifiers 130.

Figure 4:
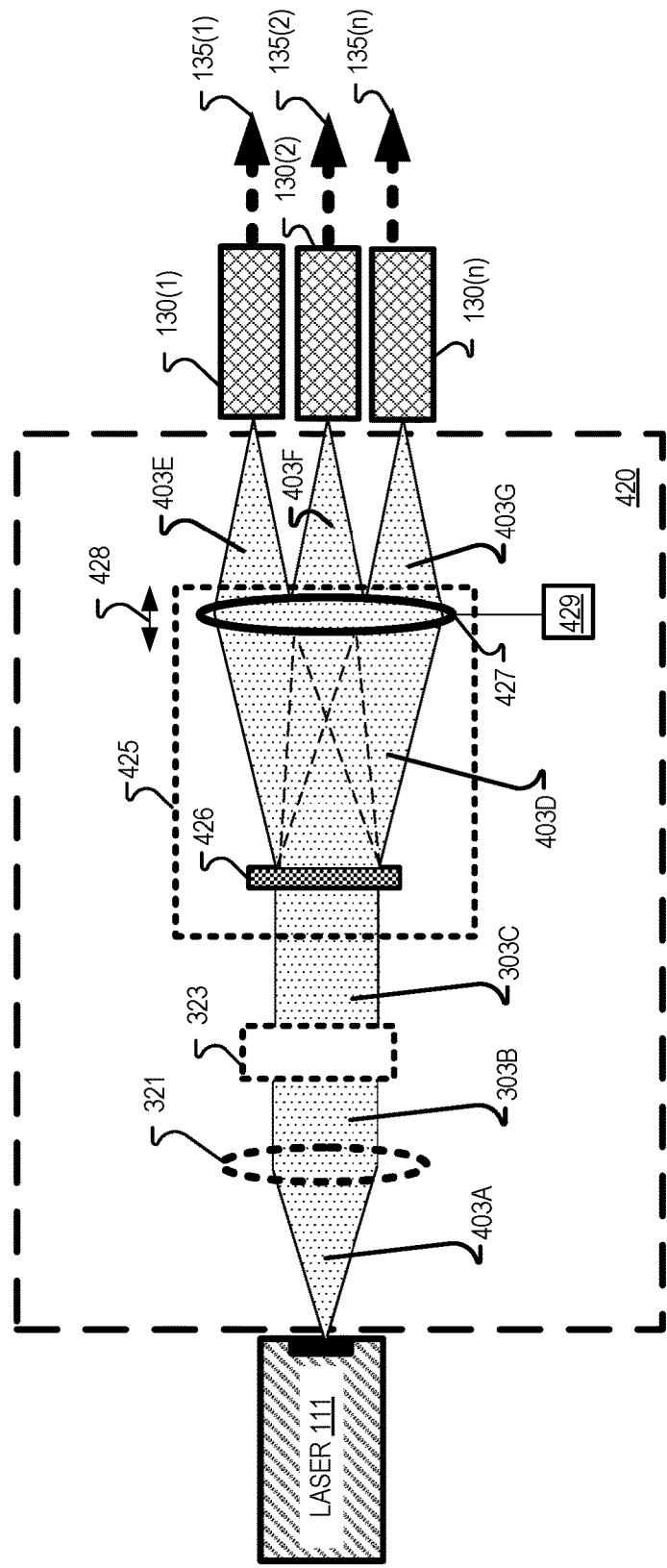
FIG. 4 illustrates an example laser assembly including a distribution optical element and a focusing optical element, in accordance with aspects of the disclosure.

FIG. 4 illustrates an example laser assembly 401 comprising an example optical assembly 420 having optical system 425 including a distribution optical element 426 and a focusing optical element 427, in accordance with aspects of the disclosure. In FIG. 4, distribution optical element 426 is configured to receive light 303C from optical isolator 323 and generate distributed beam light 403D. Distribution optical element 426 may be a diffractive optical element such as a holographic optical element or a diffractive grating. Distribution optical element 426 may be reflective or (at least partially) transmissive. Focusing optical element 427 receives the distributed beam light 403D and focuses the distributed beam light 403D to the inputs of the optical amplifiers 130 as distributed beams 403E, 403F, and 403G, in the illustrated embodiment. Distribution optical element 426 may generate distributed beams 403D that are collimated or near-collimated.

In some embodiments, focusing optical element 427 is positioned at approximately one focal length (of the focusing optical element 427) from the inputs 137 of the optical amplifiers 130. In an embodiment, focusing optical element 427 is positioned less than one focal length from the inputs to the optical amplifiers so the distributed beams are defocused and a beam spot of the distributed beams slightly over-illuminates input apertures of the inputs of the optical amplifiers. Slightly over-illuminating the input apertures to the optical amplifiers may relieve some tolerance constraints since the input aperture will be fully illuminated by the distributed beam as long as the input aperture is positioned so that the beam spot illuminates the entire input aperture. In one embodiment, focusing optical element 427 is positioned more than one focal length from the inputs to the optical amplifiers so the distributed beams slightly over-illuminate input apertures of the inputs of the optical amplifiers.

Figure 5:
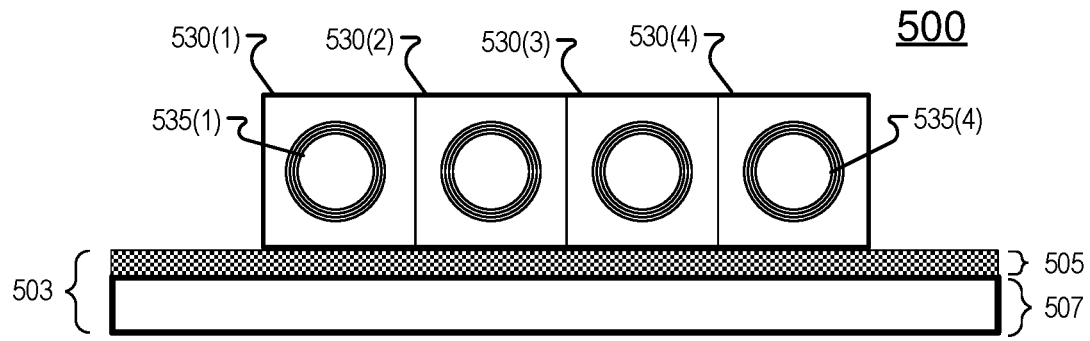
FIG. 5 illustrates an example one-dimensional array of optical amplifiers included in an optical amplifier chip, in accordance with aspects of the disclosure.

FIG. 5 illustrates an example one-dimensional array of optical amplifiers 530 included in an optical amplifier chip 500, in accordance with aspects of the disclosure. Optical amplifiers 530 are disposed on a common chip layer 503 that includes a substrate layer 505 and an optional heat-sink layer 507 to dissipate heat generated by optical amplifiers 530. Each optical amplifier 530 includes an input aperture 535, although only input apertures 535(1) and 535(4) corresponding to optical amplifiers 530(1) and 530(4), respectively, are specifically illustrated. The optical amplifiers 530 may be used as optical amplifiers 130. Substrate layer 505 may be patterned. Although there are only four optical amplifiers illustrated in FIG. 5, those skilled in the art understand that more or fewer optical amplifiers could be included in chip 500. For example chip 500 could include 10 or 20 optical amplifiers. Conductors (not illustrated) to facilitate driving electrical currents of the optical amplifiers may also be included in chip 500.

Figure 6:
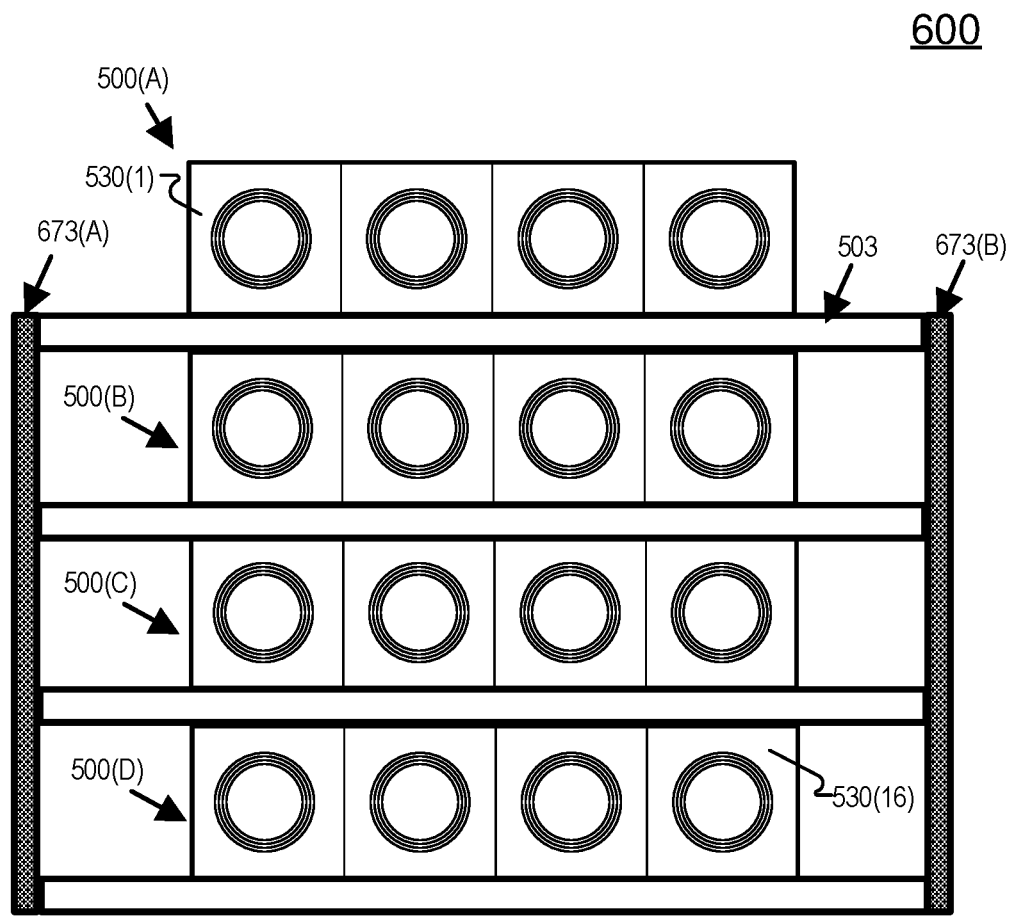
FIG. 6 illustrates a two-dimensional stacked chip that includes a plurality of optical amplifiers chips, in accordance with aspects of the disclosure.

FIG. 6 illustrates a two-dimensional stacked chip 600 that includes a plurality of optical amplifiers chips 500, in accordance with aspects of the disclosure. Two-dimensional stacked chip 600 includes chips 500A, 500B, 500C, and 500D arranged so that the one-dimensional array of optical amplifiers on the chips 500 are collectively arranged in a two-dimensional array. In the illustrated embodiment, stacked chip 600 includes a 4×4 two-dimensional array of optical amplifiers 530 where the integer number n of the optical amplifiers is 16. When the optical amplifiers are arranged in a 4×4 two-dimensional array, the distributed beams illuminating the input apertures of the optical amplifiers may also form a 4×4 two-dimensional array of distributed beams to illuminate the corresponding optical amplifiers. In some embodiments, reference optical amplifier 140 may take the place of one of the optical amplifiers 130/530 in a two-dimensional array. Stacked chip 600 may include support structures 673 to stabilize and connect the chip layers 503 of chips 500. Support structures 673 may also facilitate heat-sinking.

Figure 7:
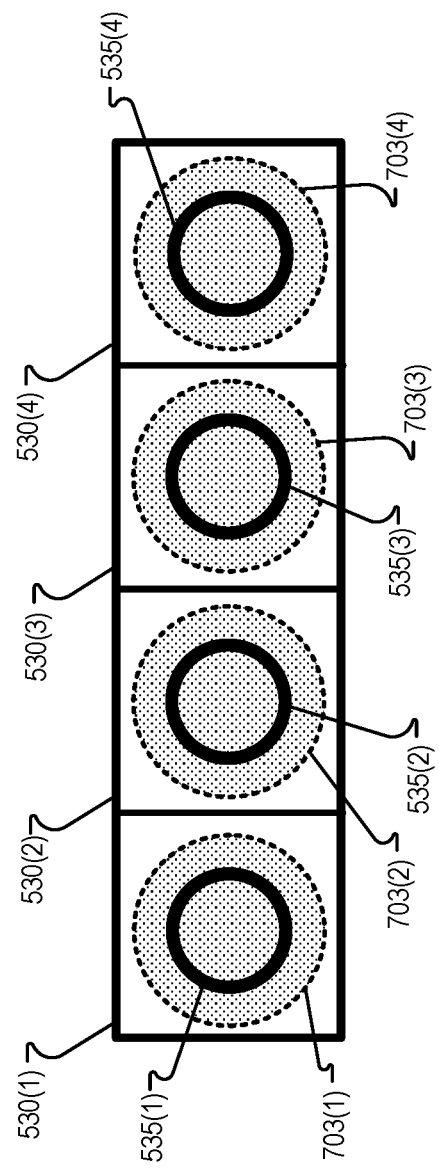
FIG. 7 illustrates example optical amplifiers having input apertures being over-illuminated by beam spots of the distributed beams generated by an optical system, in accordance with aspects of the disclosure.

FIG. 7 illustrates example optical amplifiers 530 having input apertures 535 being over-illuminated by beam spots 703 of the distributed beams generated by optical system 325 or 425. Hence, a small spatial shift of the input apertures 535 would still allow the input apertures 535 to receive the same amount of the distributed beam that illuminates the input aperture. Although the input apertures 535 in FIGS. 5-7 are illustrated as circular for description purposes, those skilled in the art understand that the input apertures may have different geometric shapes that facilitate waveguiding.

Referring to FIG. 4, focusing optical element 427 may be moved along a translation axis 428 to selectively focus and/or defocus the beam spots 703 of the distributed beams with respect to the input apertures of the optical amplifiers. In this way, selectively focusing and defocusing the distributed beams may control a beam intensity of the respective amplified infrared laser light 135 that enters diffuse medium 180. FIG. 4 illustrates an actuator 429 included in optical assembly 420 and configured to selectively move focusing optical element 427 along translation axis 428. Actuator 429 may include a micro-electro-mechanical system (MEMS) device that is responsive to an electronic control signal to move focusing optical element 427 along axis 428, for example. In the examples of FIG. 3 and FIG. 4, the illustrated optical components may be held in place by supportive structures so that assemblies 301 and 401 are considered free space optical assemblies.

Figure 8:
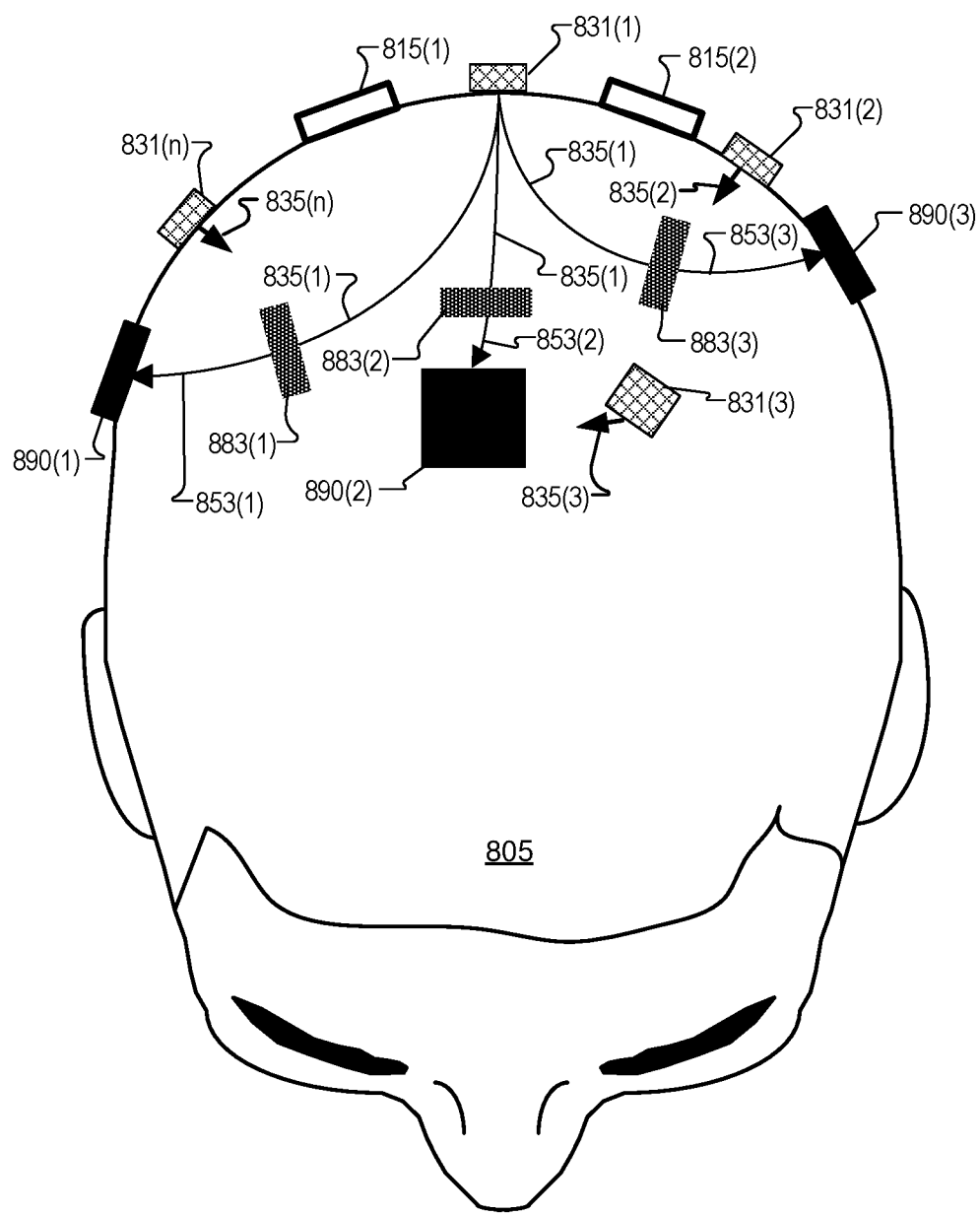
FIG. 8 illustrates an example placement of components of an imaging system with respect to a human head, in accordance with aspects of the disclosure.

FIG. 8 illustrates an example placement of components of an imaging system 800 with respect to a human head 805, in accordance with aspects of the disclosure. FIG. 8 is a top-down view of a human head 805. Imaging system 800 includes outputs 831 of optical amplifiers, imaging modules 890, and directional ultrasonic emitters 815. Imaging modules 890 may include the features of imaging module 190 and ultrasonic emitters 815 may include the features of ultrasonic emitter 115. FIG. 8 shows that amplified infrared laser light 835 is directed into head 805 by the outputs 831 of optical amplifiers (not illustrated). The optical amplifiers may include the features of optical amplifiers 130. An optical fiber may be used to route the light 835 from a chip (e.g. 500 or 600) to particular output positions with respect to head 805. In some embodiments, the outputs 831 of the optical amplifiers are spatially positioned on head 805 in positions so that each imaging module 890 is equidistant to the outputs 831. This may allow each imaging module 890 to be equally illuminated by light 835 in a theoretical context where head 805 had homogenous light scattering properties to homogenously scatter light 835.

The example optical paths of amplified infrared laser light 835(1) through voxels 883 is illustrated in FIG. 8, although the optical paths of light 835(2), 835(3), and 835(n) are not illustrated. Of course, in operation, the optical paths of light 835(1) to voxels 883 will not be as direct as the illustration because it will encounter voxels 883 via random scattering.

Amplified infrared laser light 835(1) outputted by output 831(1) of an optical amplifier 830(1) (not illustrated) scatters in head 805 and a portion encounters voxel 883(1). Light 835(2), 835(3) . . . through 835(n) may also illuminate voxel 883(1). One or more of ultrasonic emitters 815 may focus their ultrasound signal (not illustrated) to voxel 883(1) which generates a wavelength-shifted infrared exit signal 853(1) of the light 835 that illuminated voxel 883(1). Imaging module(s) 890 may capture an image of an interference pattern generated by exit signal 853(1) interfering with an infrared reference beam as a measurement of the absorption of voxel 883(1) to light 835. FIG. 8 illustrates that imaging module(s) 890 may also capture images of an interference pattern generated by exit signal 853(2) interfering with an infrared reference beam (e.g. 157) as a measurement of the absorption of voxel 883(2) to light 835 and imaging module(s) 890 may also capture images of an interference pattern generated by exit signal 853(3) interfering with an infrared reference beam as a measurement of the absorption of voxel 883(3) to light 835.

Scientific literature suggests that the penetration depth of infrared light into tissue is around 10 cm so multiple imaging modules 890 may be needed to image the entire brain or other tissue. A wearable hat may include system 800 so that system 800 can be worn as a wearable, in some embodiments. Other wearables may also include all or part of system 800.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An imaging device comprising:
   an imaging module including a sensor configured to image an interference pattern generated by an infrared reference beam interfering with an infrared exit signal exiting a diffuse medium; and
   a laser assembly comprising:
      a seed laser configured to emit seed infrared laser light;
      a plurality of optical amplifiers configured to generate amplified infrared laser light by amplifying the seed infrared laser light; and
      an optical distribution assembly configured to distribute the seed infrared laser light to inputs of the optical amplifiers in the plurality, each of the optical amplifiers configured to direct its respective amplified infrared laser light to the diffuse medium to generate the infrared exit signal.

2. The imaging device of claim 1 further comprising:
   a reference optical amplifier configured to provide infrared reference light to the imaging module to convert to the infrared reference beam by amplifying the seed infrared laser light, wherein the optical distribution assembly is configured to distribute the seed infrared laser light to a reference input of the reference optical amplifier.

3. The imaging device of claim 1, wherein the optical distribution assembly includes:
   an optical isolator configured to receive the seed infrared laser light and reduce optical feedback to the seed laser; and
   an optical system configured to receive the seed infrared laser light that has been isolated by the optical isolator and generate distributed beams illuminating the inputs of the optical amplifiers in the plurality of optical amplifiers.

4. The imaging device of claim 3, wherein the distributed beams have intensities that are approximately equal.

5. The imaging device of claim 3, wherein the optical system includes a diffractive optical element to generate the distributed beams to illuminate the inputs of the optical amplifiers.

6. The imaging device of claim 3, wherein the optical system includes:
   a distribution optical element to generate the distributed beams; and
   a focusing optical element to focus the distributed beams to the inputs of the optical amplifiers.

7. The imaging device of claim 6, wherein the focusing optical element is configured to focus the distributed beams to have a beam spot that slightly over-illuminates input apertures of the inputs of the optical amplifiers.

8. The imaging device of claim 6, wherein the optical distribution assembly includes an actuator to move the focusing optical element along a translation axis to selectively focus and defocus the distributed beams to the inputs of the optical amplifiers, wherein selectively focusing and defocusing the distributed beams controls a beam intensity of the respective amplified infrared laser light entering the diffuse medium.

9. The imaging device of claim 6, wherein the focusing optical element is positioned at approximately one focal length from the inputs of the optical amplifiers in the plurality of optical amplifiers.

10. The imaging device of claim 3 further comprising:
    a collimating optical element configured to collimate the seed infrared laser light prior to propagating to the optical isolator.

11. The imaging device of claim 1, wherein the plurality of optical amplifiers is arranged as a two-dimensional array of stacked chips, wherein each of the stacked chips includes a one-dimensional array of the optical amplifiers.

12. The imaging device of claim 1, wherein electrical drive currents that drive the plurality of optical amplifiers are synced.

13. The imaging device of claim 1, wherein the optical distribution assembly includes a plurality of optical fibers configured to guide portions of the seed infrared laser light to the plurality of optical amplifiers.

14. The imaging device of claim 1 further comprising:
    an ultrasonic emitter configured to deliver an ultrasonic signal to a given voxel of the diffuse medium while the amplified infrared laser light from the plurality of optical amplifiers illuminates the given voxel.

15. The imaging device of claim 1, wherein the seed laser is one of a fiber laser or a semiconductor laser, and wherein the sensor includes a complementary metal-oxide-semiconductor (CMOS) image sensor.

16. The imaging device of claim 1, wherein each optical amplifier in the plurality of optical amplifiers includes a frequency converter that down-coverts a first wavelength of the seed infrared laser light to a second wavelength of the amplified infrared laser light.

17. A laser device comprising:
    a seed laser configured to emit seed laser light;
    a plurality of optical amplifiers configured to generate amplified laser light by amplifying the seed laser light; and
    an optical distribution assembly configured to distribute the seed laser light to an input of each of the optical amplifiers in the plurality, each of the optical amplifiers configured to direct its respective amplified laser light to a common target, wherein an output aperture of the optical amplifiers in the plurality of optical amplifiers are gradually tapered to provide a beam quality factor of the amplified laser light that is greater than 1,000.

18. The laser device of claim 17 further comprising:
    a reference optical amplifier configured to generate reference light by amplifying the seed laser light, wherein the optical distribution assembly is configured to distribute the seed infrared laser light to a reference input of the reference optical amplifier, and wherein the reference light is not directed to the common target.

19. The laser device of claim 17, wherein the optical distribution assembly includes a diffractive optical element configured to receive the seed laser light and generate distributed beams that illuminate the inputs of the optical amplifiers in the plurality of optical amplifiers.

20. An imaging device comprising:
    an imaging module including a sensor configured to image an infrared exit signal exiting a diffuse medium; and
    a laser assembly comprising:
       a seed laser configured to emit seed infrared laser light;
       a plurality of optical amplifiers configured to generate amplified infrared laser light by amplifying the seed infrared laser light, each of the optical amplifiers configured to separately direct its respective amplified infrared laser light to the diffuse medium without being optically combined, prior to encountering the diffuse medium, with any of the other amplified infrared laser light emitted by other optical amplifiers in the plurality of optical amplifiers.

* * * * *